United States Patent [19]

Araki et al.

[11] 4,450,165

[45] May 22, 1984

[54] DIHYDROPYRIDINE COMPOUNDS

[75] Inventors: Kazuhiko Araki; Hideki Ao, both of Nakatsu; Tomohiko Kimura, Izumi; Kenichi Aihara, Yoshitomi, all of Japan

[73] Assignee: Yoshitomi Pharmaceutical Industries, Ltd., Osaka, Japan

[21] Appl. No.: 385,141

[22] Filed: Jun. 4, 1982

[30] Foreign Application Priority Data

Jun. 4, 1981 [JP] Japan ................................. 56-86383

[51] Int. Cl.³ .................... A61K 31/47; C07D 215/58; C07D 213/79
[52] U.S. Cl. .................................... 424/258; 424/251; 424/266; 546/158; 546/263; 546/268; 546/275; 546/280; 546/281; 546/278; 546/284; 544/333
[58] Field of Search ............... 546/263, 158, 275, 278, 546/280, 281, 283, 284, 268; 544/333; 424/266, 251, 258

[56] References Cited

U.S. PATENT DOCUMENTS 3,985,758 10/1976 Murakami et al. .................. 424/266
3,996,234 12/1976 Bossert et al. ....................... 424/266

FOREIGN PATENT DOCUMENTS 2935451 3/1981 Fed. Rep. of Germany .

Primary Examiner—Jane T. Fan
Attorney, Agent, or Firm—Sughrue, Mion, Zinn, Macpeak and Seas

[57] ABSTRACT

A dihydropyridine compound of the formula:

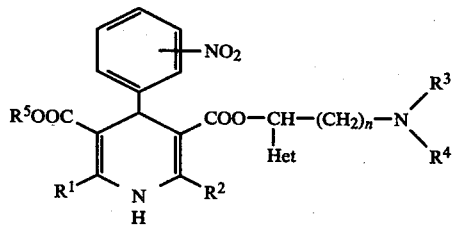

or a pharmaceutically acceptable acid addition salt thereof, wherein Het is 5- or 6-membered aromatic heteroaryl, $R^1$ and $R^2$ are each lower alkyl, $R^3$ is lower alkyl, $R^4$ is hydrogen, lower alkyl or aralkyl, $R^5$ is lower alkyl or aralkyl, and n is 1 or 2. Such compounds are useful as therapeutic agents for myocardial and cerebral ischemic syndroms and hypertension.

10 Claims, No Drawings

DIHYDROPYRIDINE COMPOUNDS

This invention relates to novel dihydropyridine compounds which are useful as therapeutic agents for myocardial and cerebral ischemic syndroms and hypertension.

According to the present invention, there is provided a 1,4-dihydropyridine-3,5-dicarboxylic acid ester compound of the formula:

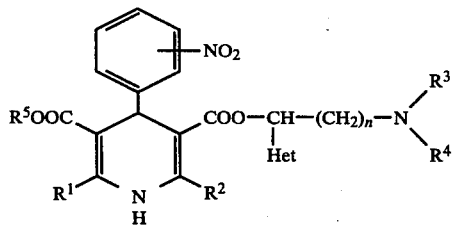

or a pharmaceutically acceptable acid addition salt thereof, wherein Het is 5- or 6-membered aromatic heteroaryl (e.g. furyl, thienyl, pyridyl, thiazolyl, oxazolyl, isoxazolyl, pyrrolyl, imidazolyl, pyrimidinyl or 3,4-dihydrocarbostyril; such heteroaryl may be substituted by lower alkyl such as methyl, halogen such as chlorine or bromine, or the like), $R^1$ and $R^2$ are each lower alkyl (e.g. methyl, ethyl, propyl, isopropyl or butyl), $R^3$ is lower alkyl such as mentioned for $R^1$, $R^4$ is hydrogen, lower alkyl such as mentioned for $R^1$ or aralkyl (e.g. benzyl, fluorobenzyl, chlorobenzyl, methoxybenzyl, dimethoxybenzyl, phenethyl, chlorophenethyl, methoxyphenethyl, 3-phenylpropyl or α-methylbenzyl), $R^5$ is lower alkyl such as mentioned for $R^1$ or aralkyl such as mentioned for $R^4$, and n is 1 or 2.

The compounds of formula (I) can be produced by one of the following methods (I) to (VI):

Method I

A method of reacting a compound of the formula:

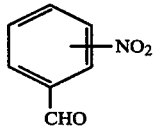

with a compound of the formula:

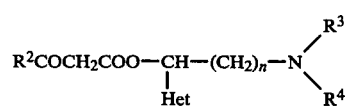

wherein Het, $R^2$, $R^3$, $R^4$ and n are as defined above, and a compound of the formula:

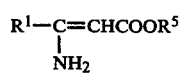

wherein $R^1$ and $R^5$ are as defined above.

The reaction is usually carried out without a solvent or in an inert solvent such as benzene, toluene, xylene, chloroform, carbon tetrachloride, methylene chloride, ethylene chloride, acetonitrile, methanol, ethanol, propanol, isopropanol, butanol or water, at room temperature or under warming or heating.

The starting compounds of formula (III) can be prepared by reacting a compound of the formula:

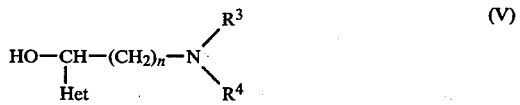

wherein Het, $R^3$, $R^4$ and n are as defined above, with diketene, without a solvent or in an inert solvent such as benzene, toluene, xylene, chloroform, carbon tetrachloride, methylene chloride, ethylene chloride, dioxane, ether or tetrahydrofuran, if necessary in the presence of a basic catalyst such as pyridine, picoline or triethylamine, at room temperature or under warming or heating.

The starting compounds of formula (IV) can be prepared by reacting a compound of the formula:

wherein $R^1$ and $R^5$ are as defined above, with ammonia or a salt thereof (e.g. ammonium chloride).

Method II

A method of reacting a compound of the formula:

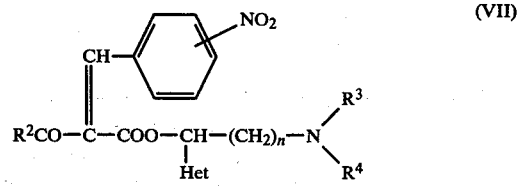

wherein Het, $R^2$, $R^3$, $R^4$ and n are as defined above, with a compound of formula (IV) mentioned above.

The reaction is usually carried out under the conditions mentioned in Method I.

The starting compounds of formula (VII) can be prepared by reacting a compound of formula (II) with a compound of formula (III) in a suitable solvent such as benzene, toluene or xylene, preferably in the presence of an acid catalyst such as sulfuric acid, phosphoric acid, formic acid, acetic acid, ethanesulfonic acid or p-toluenesulfonic acid, under heating.

Method III

A method of reacting a compound of the formula:

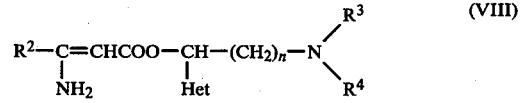

wherein Het, $R^2$, $R^3$, $R^4$ and n are as defined above, with a compound of formula (II) and a compound of formula (VI).

The reaction is usually carried out under the conditions mentioned in Method I.

The starting compounds of formula (VIII) can be prepared by reacting a compound of formula (III) with ammonia or a salt thereof (e.g. ammonium chloride).

Method IV

A method of reacting a compound of the formula:

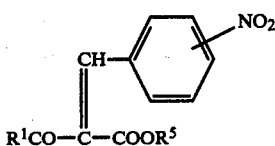
(IX)

wherein $R^1$ and $R^5$ are as defined above, with a compound of formula (VIII).

The reaction is usually carried out under the conditions mentioned in Method I.

The starting compounds of formula (IX) can be prepared by reacting a compound of formula (II) with a compound of formula (VI). It is not always necessary to isolate the thus obtained compounds of formula (IX).

Method V

A method of reacting a compound of the formula:

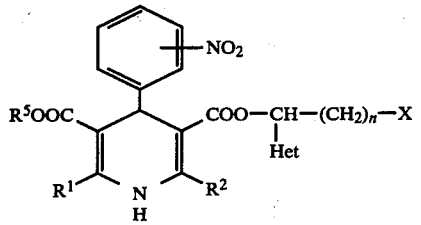
(X)

wherein Het, $R^1$, $R^2$, $R^5$ and n are as defined above, and X is a reactive acid ester residue such as halogen (Cl, Br or I), alkylsulfonyloxy (e.g. methylsulfonyloxy or ethylsulfonyloxy) or arylsulfonyloxy (e.g. phenylsulfonyloxy or p-tolylsulfonyloxy), with a compound of the formula:

(XI)

wherein $R^3$ and $R^4$ are as defined above.

The reaction is usually carried out in a solvent such as mentioned for Method I, in the presence of an acid acceptor such as potassium carbonate, sodium carbonate, sodium hydrogen carbonate, triethylamine, dimethylaniline, diethylaniline or pyridine, at a temperature of from room temperature to the boiling point of the solvent employed.

The starting compounds of formula (X) can be prepared, for example, by one of Methods I to IV, using a compound of the formula:

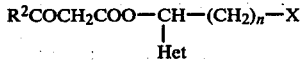
(XII)

wherein Het, $R^2$, n and X are as defined above, as a starting material.

Method VI

A method of reacting a compound of the formula:

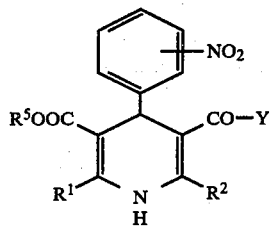
(XIII)

wherein $R^1$, $R^2$ and $R^5$ are as defined above, and Y is halogen atom, with a compound of formula (V) mentioned above.

The reaction is usually carried out in an inert solvent such as benzene, toluene, xylene, chloroform, carbon tetrachloride, methylene chloride, ethylene chloride, dioxane, ether or tetrahydrofuran, at a temperature below room temperature.

The starting compounds of formula (XIII) can be prepared in accordance with the method described in "Chem. Pharm. Bull.", 28(9), 2609–2613 (1980) by treating the corresponding carboxylic acid with a halogenating agent such as phosphorus oxychloride, phosphorus oxybromide, phosphorus trichloride, phosphorus pentachloride or thionyl chloride.

Preparation of Starting Compounds (1) Starting Compounds of Formula (V)

2-(Bromoacetyl)furan (95 g) is added slowly to a stirred mixture of 75 g of N-methylbenzylamine and 70 g of potassium carbonate in 300 ml of methanol at 20°–30° C. The mixture is stirred at room temperature for 2.5 hours, and the insoluble matter is filtered off. To the filtrate is added 20 g of sodium borohydride at 10°–20° C. with stirring, and the mixture is stirred at room temperature for 3 hours. The solvent is then distilled off under reduced pressure, water is added to the residue, and the separated oil is extracted with ethyl acetate. The extract is washed with water, dried over anhydrous magnesium sulfate, and concentrated under reduced pressure. Distillation of the residue gives 80 g of 2-(N-benzyl-N-methylamino)-1-(2-furyl)ethanol as pale yellow viscous oil, boiling at 130°–138° C. (0.2 mmHg).

The following compounds are similarly prepared, for example.

2-(N-benzyl-N-methylamino)-1-(2-thienyl)ethanol, b.p. 124°–126° C. (0.05 mmHg);
2-(N-benzyl-N-methylamino)-1-(3-thienyl)ethanol, b.p. 137°–145° C. (0.05 mmHg); and
2-diethylamino-1-(2-thienyl)ethanol, b.p. 78°–80° C. (0.07 mmHg).

(2) Starting Compounds of Formula (III)

A mixture of 23.1 g of 2-(N-benzyl-N-methylamino)-1-(2-furyl)ethanol and 10.1 g of diketene in 150 ml of benzene is refluxed for 3 hours. After cooling, the solvent is distilled off under reduced pressure. The residue [2-(N-benzyl-N-methylamino)-1-(2-furyl)ethyl acetoacetate] is used to the next reaction without purification.

The compounds of the invention represented by formula (I) have at least two asymmetric carbon atoms and are present as stereoisomers or as mixtures of these isomers. All of these are within the scope of the present invention. A mixture of the isomers, if desired, may be separated into the diastereomers of the individual optical isomers in a conventional manner such as recrystallization, column chromatography, distillation or optical resolution. When a starting compound is used in an optically active form, the compounds of formula (I) can be produced stereo-selectively.

The compounds of formula (I) can form pharmaceutically acceptable acid addition salts with various inorganic and organic acids such as hydrochloric, hydrobromic, phosphoric, sulfuric, maleic, fumaric, tartaric and acetic acids.

The compounds of formula (I) and pharmaceutically acceptable acid addition salts thereof show potent and long-lasting vasodilating and antihypertensive activities. The present invention has been accomplished on the basis of the new finding that the introduction of the heteroaryl group represented by Het at α-position of the aminoalkylester moiety brings about remarkably prolonged duration of such activities.

Pharmacological Properties

1. Test compounds

A: 2,6-Dimethyl-4-(m-nitrophenyl)-1,4-dihydropyridine-3,5-dicarboxylic acid-3-methylester-5-[2-(N-benzyl-N-methylamino)-1-(2-furyl)ethyl]ester hydrochloride (β-diastereoisomer of Example 1)

B: 2,6-Dimethyl-4-(m-nitrophenyl)-1,4-dihydropyridine-3,5-dicarboxylic acid-3-methylester-5-[2-(N-benzyl-N-methylamino)-1-(2-thienyl)ethyl]ester hydrochloride (β-diastereoisomer of Example 2)

Nicardipine (Comparison): 2,6-Dimethyl-4-(m-nitrophenyl)-1,4-dihydropyridine-3,5-dicarboxylic acid-3-methylester-5-[2-(N-benzyl-N-methylamino)ethyl]-ester hydrochloride.

2. Methods and Results (1) Hypotensive activity

Five male spontaneously hypertensive rats were used for each experiment. Systolic blood pressure was determined using an indirect tail cuff method before and at 1, 3, 5 and 7 hours following the oral administration of the test compound. Effective dose ($ED_{30}$) which showed the maximum hypotension by 30 mmHg was estimated from the dose response curve. The results are shown in Table 1.

TABLE 1

| Test Compound | $ED_{30}$ (mg/kg) |
|---|---|
| A | 1.3 |
| B | 1.0 |
| Nicardipine | 5.0 |

(2) Effect on vertebral blood flow

Adult mongrel dogs were anesthetized with sodium pentobarbital (25 mg/kg, i.v.) and heparinized (500 U/kg, i.v.). Under the artificial ventilation, the right vertebral artery was perfused with the arterial blood from the left carotid artery through a short bypass. The perfused flow was measured by means of an electromagnetic flow-meter. The test compound was dissolved in an aqueous solution containing 0.1% dimethyl sulfoxide and 0.01% polyoxyethylene hydrogenated castor oil (cremophor EL ®), and injected into the afferent tube. The percentage increase in blood flow by papaverine 100 μg was taken as 100%. Effective dose of test compound in blood flow was obtained graphically from the dose response curve as $ED_{100}$. The duration was measured as the time for which the half maximum response remained. The results are shown in Table 2.

TABLE 2

| Test Compound | $ED_{100}$ (μg) | Duration (min.) |
|---|---|---|
| A | 1.0 | 11.0 |
| B | 1.8 | 22.5 |
| Nicardipine | 0.4 | 1.0 |
| Papaverine | 100 | 0.4 |

(3) Effect on coronary blood flow

Adult mongrel dogs were anesthetized with sodium pentbarbital (30–35 mg/kg, i.v.) and heparinized (300 U/kg, i.v.). Under the artificial ventilation, the left coronary artery was perfused with the arterial blood from the right femoral artery through the special cannula according to the technique of Yago: Folia Pharmacologica Japonica, 57, 380 (1961). The perfused flow was measured by means of an electromagnitic flow-meter. The test compound was dissolved in an aqueous solution containing 15% ethanol and 15% polyethylene glycol, and injected into the afferent cannula. The percentage increase in blood flow by nifedipine 10 μg was taken as 100%. Effective dose of test compound in blood flow was obtained graphically from the dose response curve as $ED_{50}$. The duration was measured as the time for which the half maximum response remained. The results are shown in Table 3.

TABLE 3

| Test Compound | $ED_{50}$ (μg) | Duration (min.) |
|---|---|---|
| A | 1.5 | 15.0 |
| Nicardipine | 0.5 | 3.0 |
| (Nifedipine) | (0.5) | (2.0) |

In view of various tests including those mentioned above, the compounds of the invention represented by formula (I), in base or salt form, can be safely administered as therapeutic agents for myocardial and cerebral ischemic syndroms and hypertension in the form of a pharmaceutical preparation with a suitable and conventional pharmaceutically acceptable carrier, without adversely affecting the patients.

The pharmaceutical preparations can take any conventional form such as tablets, capsules, granules, powders or injectable solutions.

The following is an example of formulations when a compound of the invention is administered for pharmaceutical purposes:

Tablets (5 mg) are prepared from the following compositions:

| | |
|---|---|
| β-Diastereoisomer of Example 1 | 5.0 mg |
| Lactose | 62.3 mg |
| Cornstarch | 25.0 mg |
| Microcrystalline Cellulose | 6.0 mg |
| Methyl Cellulose | 1.0 mg |
| Magnesium Stearate | 0.7 mg |
| | 100.0 mg |

Powders (1% by weight) are prepared from the following compositions:

| | |
|---|---|
| β-Diastereoisomer of Example 1 | 1% |
| Lactose | 88% |
| Microcrystalline Cellulose | 10% |
| Methyl Cellulose | 1% |
| | 100% |

The daily dose of compound (I) or a salt thereof for human adults usually ranges from about 1 mg to about 50 mg for oral administration, in single or multiple dose, but it may vary depending upon the age, body weight, and/or severity of the conditions to be treated as well as the response to the medication.

The present invention will be better understood from the following examples, but they are not to be construed as limiting the present invention.

In the following examples, when two kinds of diastereoisomers are obtained, the diastereoisomer which shows a spot appearing at the upper part by thin layer chromatography is referred to as "α-diastereoisomer" and the diastereoisomer which shows a spot appearing at the lower part is referred to as "β-diastereoisomer".

EXAMPLE 1

2,6-Dimethyl-4-(m-nitrophenyl)-1,4-dihydropyridine-3,5-dicarboxylic acid-3-methylester-5-[2-(N-benzyl-N-methylamino)-1-(2-furyl)ethyl]ester (1) A mixture of 7.5 g of m-nitrobenzaldehyde, 15 g of 2-(N-benzyl-N-methylamino)-1-(2-furyl)ethyl acetoacetate and 6 g of methyl β-aminocrotonate in 150 ml of ethanol is refluxed for 20 hours. The reaction mixture is then concentrated under reduced pressure, and the residue is dissolved in ethyl acetate. The solution is washed with water and concentrated under reduced pressure. The residue is purified by column chromatography on silica gel. The firstly eluted product is dissolved in ethanol whereupon a saturated solution of hydrogen chloride in ethanol is added. The precipitated crystals are collected by filtration and recrystallized from ethanol to give 3 g of α-diastereoisomer of the title compound in the form of the hydrochloride as pale yellow crystals, melting at 178°–180° C. with decomposition. The lastly eluted product is treated in the same manner mentioned above to give 5 g of β-diastereoisomer of the title compound in the form of the hydrochloride as pale yellow crystals, melting at 195°–198° C. with decomposition.

(2) A mixture of 22.4 g of 2-(N-benzyl-N-methylamino)-1-(2-furyl)ethyl m-nitrobenzilideneacetoacetate and 6 g of methyl β-aminocrotonate in 200 ml of isopropanol is refluxed for 20 hours. The reaction mixture is then concentrated under reduced pressure. The residue is purified by column chromatography on silica gel. The firstly eluted product is dissolved in acetone whereupon a saturated solution of hydrogen chloride in ethanol is added, and the mixture is allowed to stand. The precipitated crystals are collected by filtration and recrystallized from ethanol to give 2.7 g of α-diastereoisomer of the title compound in the form of the hydrochloride as pale yellow crystals, melting at 178°–180° C. with decomposition. The lastly eluted product is treated in the same manner mentioned above to give 4.5 g of β-diastereoisomer of the title compound in the form of the hydrochloride as pale yellow crystals, melting at 195°–198° C. with decomposition.

(3) A mixture of 16 g of 2-(N-benzyl-N-methylamino)-1-(2-furyl)ethyl β-aminocrotonate, 8 g of m-nitrobenzaldehyde and 6 g of methyl acetoacetate in 250 ml of ethanol is refluxed for 24 hours. The reaction mixture is then concentrated under reduced pressure. The residue is purified by column chromatography on silica gel. The firstly eluted product is dissolved in acetone whereupon a saturated solution of hydrogen chloride in ethanol is added, and the mixture is allowed to stand. The precipitated crystals are collected by filtration and recrystallized from ethanol to give 3.5 g of α-diastereoisomer of the title compound in the form of the hydrochloride as pale yellow crystals, melting at 178°–180° C. with decomposition. The lastly eluted product is treated in the same manner mentioned above to give 5 g of β-diastereoisomer of the title compound in the form of the hydrochloride as pale yellow crystals, melting at 195°–198° C. with decomposition.

(4) A mixture of 13 g of methyl m-nitrobenzylideneacetoacetate and 16 g of 2-(N-benzyl-N-methylamino)-1-(2-furyl)ethyl β-aminocrotonate in 200 ml of isopropanol is refluxed for 20 hours. The reaction mixture is then concentrated under reduced pressure, and the residue is dissolved in toluene whereupon 2N-hydrochloric acid is added. The separated oil is neutralized with sodium carbonate solution and extracted with ethyl acetate. The extract is dried over anhydrous magnesium sulfate, and the solvent is distilled off under reduced pressure. The residue is purified by column chromatography on silica gel. The firstly eluted product is dissolved in acetone whereupon a saturated solution of hydrogen chloride in ethanol is added, and the mixture is allowed to stand. The precipitated crystals are collected by filtration and recrystallized from ethanol to give 3.1 g of α-diastereoisomer of the title compound in the form of the hydrochloride as pale yellow crystals, melting at 178°–180° C. with decomposition. The lastly eluted product is treated in the same manner mentioned above to give 4.6 g of β-diastereoisomer of the title compound in the form of the hydrochloride as pale yellow crystals, melting at 195°–198° C. with decomposition.

(5) A mixture of 23 g of 2,6-dimethyl-4-(m-nitrophenyl)-1,4-dihydropyridine-3,5-dicarboxylic acid-3-methylester-5-[2-chloro-1-(2-furyl)ethyl]ester, 8 g of N-methylbenzylamine and 10 g of potassium carbonate in 150 ml of dimethylformamide is stirred at 70°–80° C. for 24 hours. The insoluble matter is then filtered off, and the filtrate is concentrated under reduced pressure. The residue is dissolved in ethyl acetate. The solution is washed with water, dried over anhydrous magnesium sulfate, and concentrated under reduced pressure. The residue is purified by column chromatography on silica gel. The firstly eluted product is dissolved in acetone whereupon a saturated solution of hydrogen chloride in ethanol is added, and the mixture is allowed to stand. The precipitated crystals are collected by filtration and recrystallized from ethanol to give 2.2 g of α-diastereoisomer of the title compound in the form of the hydrochloride as pale yellow crystals, melting at 178°–180° C. with decomposition. The lastly eluted product is treated in the same manner mentioned above to give 4.0 g of β-diastereoisomer of the title compound in the form of the hydrochloride as pale yellow crystals, melting at 195°–198° C. with decomposition.

(6) The title compound which is represented by the formula:

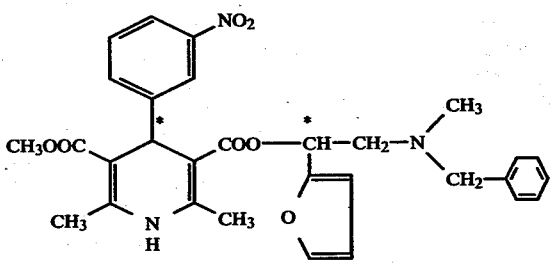

wherein the asterisks indicate asymmetric carbon atoms, has two asymmetric carbon atoms, and therefore four kinds of stereoisomers exist. These isomers are produced as follows, for example.

Phosphorus pentachloride (14.7 g) is added at once to a suspension of 21.2 g of (−)-5-methoxycarbonyl-2,6-dimethyl-4-(m-nitrophenyl)-1,4-dihydropyridine-3-carboxylic acid in 300 ml of methylene chloride under cooling at −10° C. on a dry ice-methanol bath. The resulting mixture is stirred at room temperature for 3 hours and then cooled to −30° C. whereupon a solution of 44.5 g of 2-(N-benzyl-N-methylamino)-1-(2-furyl)ethanol in 100 ml of methylene chloride is added slowly, and the whole is stirred under cooling on an ice bath for 2 hours. The reaction mixture is then made alkaline with an aqueous sodium carbonate solution. The methylene chloride layer is washed successively with water, 2N-hydrochloric acid, an aqueous sodium carbonate solution, and water, dried over anhydrous magnesium sulfate, and concentrated under reduced pressure. The residue is chromatographed over silica gel with chloroform-ethyl acetate eluants. The firstly eluted product is $\alpha_1$-isomer of the title compound, and the lastly eluted product is $\beta_1$-isomer.

Using (+)-5-methoxycarbonyl-2,6-dimethyl-4-(m-nitrophenyl)-1,4-dihydropyridine-3-carboxylic acid, $\alpha_2$- and $\beta_2$-isomers are also produced.

These isomers are summarized below:

| $\alpha$-Diastereoisomer | $\alpha_1$-Isomer | m.p. 110–112° C. (methanol) $[\alpha]_D$ + 35.6 (c 0.5, methanol) |
|---|---|---|
| | $\alpha_2$-Isomer | m.p. 111–113° C. (methanol) $[\alpha]_D$ − 38.6 (c 0.5, methanol) |
| $\beta$-Diastereoisomer | $\beta_1$-Isomer | amorphous $[\alpha]_D$ + 4.85 (c 0.5, methanol) |
| | $\beta_2$-Isomer | amorphous $[\alpha]_D$ − 16.02 (c 0.5, methanol) |

EXAMPLE 2

2,6-Dimethyl-4-(m-nitrophenyl)-1,4-dihydropyridine-3,5-dicarboxylic acid-3-methylester-5-[2-(N-benzyl-N-methylamino)-1-(2-thienyl)-ethyl]ester A mixture of 8.6 g of m-nitrobenzaldehyde, 18.9 g of 2-(N-benzyl-N-methylamino)-1-(2-thienyl)ethyl acetoacetate and 6.6 g of methyl $\beta$-aminocrotonate in 80 ml of ethanol is refluxed for 16 hours. The reaction mixture is then concentrated under reduced pressure, and the residue is dissolved in ethyl acetate. The solution is washed with water and concentrated under reduced pressure. The residue is dissolved in acetone whereupon a saturated solution of hydrogen chloride in ethanol is added. A small amount of ether is then added until the solution becomes cloudy, and the whole is allowed to stand. The precipitated crystals are collected by filtration and recrystallized from methanol to give 8 g of $\beta$-diastereoisomer of the title compound in the form of the hydrochloride as pale yellow crystals, melting at 195°–197° C. with decomposition. The crystals separated out from the mother liquer are collected by filtration and recrystallized from a small amount of ethanol to give $\alpha$-diastereoisomer of the title compound in the form of the hydrochloride as pale yellow crystals, melting at 183°–185° C. with decomposition.

EXAMPLE 3

2,6-Dimethyl-4-(m-nitrophenyl)-1,4-dihydropyridine-3,5-dicarboxylic acid-3-methylester-5-[2-(N-benzyl-N-methylamino)-1-(2-pyridyl)ethyl]ester A mixture of 1.9 g of m-nitrobenzaldehyde, 4.3 g of 2-(N-benzyl-N-methylamino)-1-(2-pyridyl)ethyl acetoacetate and 1.5 g of methyl $\beta$-aminocrotonate in 20 ml of isopropanol is refluxed for 8.5 hours. The reaction mixture is then concentrated under reduced pressure. The residue is dissolved in 50 ml of isopropanol and 20 ml of ether whereupon a saturated solution of hydrogen chloride in ethanol is added. The precipitated crystals are collected by filtration, washed with ether, dissolved in methanol, and filtered off with activated charcoal. The filtrate is poured into ether. The precipitated crystals are collected by filtration, washed with ether, and dried to give the title compound in the form of the hydrochloride, melting at 160° C. with decomposition.

EXAMPLE 4

2,6-Dimethyl-4-(m-nitrophenyl)-1,4-dihydropyridine-3,5-dicarboxylic acid-3-methylester-5-[2-(N-benzyl-N-methylamino)-1-(3-pyridyl)ethyl]ester A mixture of 11.2 g of m-nitrobenzaldehyde, 24.1 g of 2-(N-benzyl-N-methylamino)-1-(3-pyridyl)ethyl acetoacetate and 8.5 g of methyl $\beta$-aminocrotonate in 100 ml of ethanol is refluxed for 19 hours. The reaction mixture is then concentrated under reduced pressure, the residue is dissolved in 100 ml of toluene, and the solution is shaken well with 50 ml of 3N-hydrochloric acid. The jelly-like substance thus obtained is added to an aqueous potassium carbonate solution and extracted with ethyl acetate. The extract is washed with water, dried over anhydrous magnesium sulfate, and concentrated under reduced pressure. The residue is dissolved in ethanol whereupon a saturated solution of hydrogen chloride in isopropanol is added, and the whole is allowed to stand. The precipitated crystals are collected by filtration and recrystallized from methanol to give the title compound in the form of the dihydrochloride, melting at 217°–220° C. with decomposition.

EXAMPLE 5

2,6-Dimethyl-4-(m-nitrophenyl)-1,4-dihydropyridine-3,5-dicarboxylic acid-3-methylester-5-[2-(N-benzyl-N-methylamino)-1-(4-pyridyl)ethyl]ester A mixture of 5.6 g of m-nitrobenzaldehyde, 12 g of 2-(N-benzyl-N-methylamino)-1-(4-pyridyl)ethyl acetoacetate and 4.2 g of methyl $\beta$-aminocrotonate in 120 ml of ethanol is refluxed for 4 hours. The reaction mixture is then concentrated under reduced pressure. The residue is purified by column chromatography on silica gel with chloroform-methanol eluants. The fraction thus obtained is concentrated under reduced pressure. The residue is dissolved in ether whereupon a saturated solution of hydrogen chloride in ethanol is added, and the whole is allowed to stand. The precipitated crystals are collected by filtration and recrystallized from a mixture of acetone and ethanol to give the title compound in the form of the dihydrochloride, melting at 154°–157° C. with decomposition.

EXAMPLE 6

2,6-Dimethyl-4-(m-nitrophenyl)-1,4-dihydropyridine-3,5-dicarboxylic acid-3-methylester-5-[2-(N-benzyl-N-methylamino)-1-(3-thienyl)ethyl]ester A mixture of 12.8 g of m-nitrobenzaldehyde, 30.5 g of 2-(N-benzyl-N-methylamino)-1-(3-thienyl)ethyl acetoacetate and 9.8 g of methyl β-aminocrotonate in 130 ml of ethanol is refluxed for 16 hours. The reaction mixture is then concentrated under reduced pressure, the residue is dissolved in 100 ml of benzene, and the solution is shaken well with 50 ml of 3N-hydrochloric acid. The jelly-like substance thus obtained is added to an aqueous potassium carbonate solution and extracted with ethyl acetate. The extract is washed with water, dried over anhydrous magnesium sulfate, and concentrated under reduced pressure. The residue is purified by column chromatography on silica gel with chloroform-methanol eluants. The firstly eluted product is dissolved in acetone whereupon a saturated solution of hydrogen chloride in ethanol is added, and the whole is allowed to stand. The precipitated crystals are collected by filtration and recrystallized from ethanol to give α-diastereoisomer of the title compound in the form of the hydrochloride, melting at 185°–187° C. The lastly eluted product is treated in the same manner mentioned above to give β-diastereoisomer of the title compound in the form of the hydrochloride, melting at 193°–195° C.

EXAMPLE 7

2,6-Dimethyl-4-(m-nitrophenyl)-1,4-dihydropyridine-3,5-dicarboxylic acid-3-methylester-5-[2-diethylamino-1-(2-thienyl)ethyl]ester A mixture of 17 g of m-nitrobenzaldehyde, 32 g of 2-diethylamino-1-(2-thienyl)ethyl acetoacetate and 13 g of methyl β-aminocrotonate in 200 ml of isopropanol is refluxed for 16 hours. The reaction mixture is then concentrated under reduced pressure, the residue is dissolved in 100 ml of toluene, and the solution is washed with water and shaken well with 50 ml of 2N-hydrochloric acid. The jelly-like substance thus obtained is added to an aqueous potassium carbonate solution and extracted with ethyl acetate. The extract is washed with water, dried over anhydrous magnesium sulfate, and concentrated under reduced pressure. The residue is purified by column chromatography on silica gel with chloroform-ethyl acetate eluants. The firstly eluted product is dissolved in acetone whereupon a saturated solution of hydrogen chloride in ethanol is added, and the whole is allowed to stand. The precipitated crystals are collected by filtration and recrystallized from ethanol to give α-diastereoisomer of the title compound in the form of the hydrochloride, melting at 208° C. with decomposition. The lastly eluted product is treated in the same manner mentioned above to give β-diastereoisomer of the title compound in the form of the hydrochloride, melting at 208° C. with decomposition (from methanol).

Using the procedures set forth in the above examples, the following compounds are also produced:

(1) 2,6-Dimethyl-4-(m-nitrophenyl)-1,4-dihydropyridine-3,5-dicarboxylic acid-3-methylester-5-[2-(N-benzyl-N-methylamino)-1-(1-methyl-3,4-dihydrocarbostyril-6-yl)ethyl]ester hydrochloride monohydrate, α-diastereoisomer: m.p. 195°–197° C. (decomposition); β-diastereoisomer: m.p. 165°–168° C. (decomposition)

(2) 2,6-Dimethyl-4-(m-nitrophenyl)-1,4-dihydropyridine-3,5-dicarboxylic acid-3-methylester-5-[2-(N-benzyl-N-methylamino)-1-(2-imidazolyl)ethyl]ester (3) 2,6-Dimethyl-4-(m-nitrophenyl)-1,4-dihydropyridine-3,5-dicarboxylic acid-3-methylester-5-[2-(N-benzyl-N-methylamino)-1-(4-methyl-5-imidazolyl)ethyl]ester (4) 2,6-Dimethyl-4-(o-nitrophenyl)-1,4-dihydropyridine-3,5-dicarboxylic acid-3-methylester-5-[2-(N-benzyl-N-methylamino)-1-(2-thienyl)ethyl]ester (5) 2,6-Dimethyl-4-(m-nitrophenyl)-1,4-dihydropyridine-3,5-dicarboxylic acid-3-isopropylester-5-[2-(N-benzyl-N-methylamino)-1-(2-thienyl)ethyl]ester (6) 2,6-Dimethyl-4-(m-nitrophenyl)-1,4-dihydropyridine-3,5-dicarboxylic acid-3-benzylester-5-[2-(N-benzyl-N-methylamino)-1-(2-thienyl)ethyl]ester (7) 2,6-Dimethyl-4-(m-nitrophenyl)-1,4-dihydropyridine-3,5-dicarboxylic acid-3-methylester-5-[2-(N-benzyl-N-methylamino)-1-(3-furyl)ethyl]ester (8) 2,6-Dimethyl-4-(m-nitrophenyl)-1,4-dihydropyridine-3,5-dicarboxylic acid-3-methylester-5-[2-(N-benzyl-N-methylamino)-1-(2-thiazolyl)ethyl]ester (9) 2,6-Dimethyl-4-(m-nitrophenyl)-1,4-dihydropyridine-3,5-dicarboxylic acid-3-methylester-5-[2-(N-benzyl-N-methylamino)-1-(2-oxazolyl)ethyl]ester

(10) 2,6-Dimethyl-4-(m-nitrophenyl)-1,4-dihydropyridine-3,5-dicarboxylic acid-3-methylester-5-[2-(N-benzyl-N-methylamino)-1-(2-pyrrolyl)ethyl]ester

(11) 2,6-Dimethyl-4-(m-nitrophenyl)-1,4-dihydropyridine-3,5-dicarboxylic acid-3-methylester-5-[2-(N-benzyl-N-methylamino)-1-(1-methyl-2-pyrrolyl)ethyl]ester

(12) 2,6-Dimethyl-4-(m-nitrophenyl)-1,4-dihydropyridine-3,5-dicarboxylic acid-3-methylester-5-[3-(N-benzyl-N-methylamino)-1-(2-thienyl)propyl]ester While the invention has been described in detail and with reference to specific embodiments thereof, it is apparent that various alterations and modifications can be made without departing from the spirit and scope thereof.

What is claimed is:

1. A dihydropyridine compound of the formula:

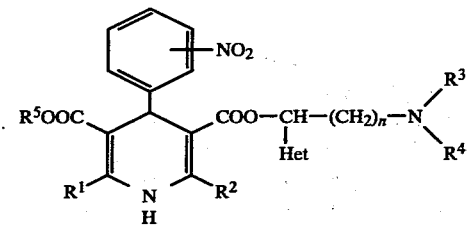

or a pharmaceutically acceptable acid addition salt thereof, wherein Het is 5- or 6-membered aromatic heteroaryl selected from the group consisting of furyl, thienyl, pyridyl, thiazolyl, oxazolyl, isooxazolyl, pyrrolyl, imidazolyl, pyrimidinyl or 3,4-dihydrocarbostyril, and said heteroaryl being unsubstituted or substituted by a lower alkyl or halogen, $R^1$ and $R^2$ are each lower alkyl, $R^3$ is lower alkyl, $R^4$ is hydrogen, lower alkyl or aralkyl, $R^5$ is lower alkyl or aralkyl, and n is 1 or 2.

2. The compound of claim 1: 2,6-dimethyl-4-(m-nitrophenyl)-1,4-dihydropyridine-3,5-dicarboxylic acid-3-methylester-5-[2-(N-benzyl-N-methylamino)-1-(2-furyl)ethyl]ester.

3. The compound of claim 1: 2,6-dimethyl-4-(m-nitrophenyl)-1,4-dihydropyridine-3,5-dicarboxylic acid-3-methylester-5-[2-(N-benzyl-N-methylamino)-1-(2-thienyl)ethyl]ester.

4. The compound of claim 1: 2,6-dimethyl-4-(m-nitrophenyl)-1,4-dihydropyridine-3,5-dicarboxylic acid-3- methylester-5-[2-(N-benzyl-N-methylamino)-1-(2-pyridyl)ethyl]ester.

5. The compound of claim 1: 2,6-dimethyl-4-(m-nitrophenyl)-1,4-dihydropyridine-3,5-dicarboxylic acid-3-methylester-5-[2-(N-benzyl-N-methylamino)-1-(3-pyridyl)ethyl]ester.

6. The compound of claim 1: 2,6-dimethyl-4-(m-nitrophenyl)-1,4-dihydropyridine-3,5-dicarboxylic acid-3-methylester-5-[2-(N-benzyl-N-methylamino)-1-(4-pyridyl)ethyl]ester.

7. The compound of claim 1: 2,6-dimethyl-4-(m-nitrophenyl)-1,4-dihydropyridine-3,5-dicarboxylic acid-3-methylester-5-[2-(N-benzyl-N-methylamino)-1-(3-thienyl)ethyl]ester.

8. The compound of claim 1: 2,6-dimethyl-4-(m-nitrophenyl)-1,4-dihydropyridine-3,5-dicarboxylic acid-3-methylester-5-[2-diethylamino-1-(2-thienyl)ethyl]ester.

9. The compound of claim 1: 2,6-dimethyl-4-(m-nitrophenyl)-1,4-dihydropyridine-3,5-dicarboxylic acid-3-methylester-5-[2-(N-benzyl-N-methylamino)-1-(1-methyl-3,4-dihydrocarbostyril-6-yl)ethyl]ester.

10. A pharmaceutical composition for use in the treatment of myocardial and cerebral ischemic syndromes and hypertension comprising the compound of claim 1 in combination with a pharmaceutically acceptable inert carrier, said compound being present in a therapeutically effective amount.

* * * * *